United States Patent [19]
Ben-Menachem

[11] Patent Number: 5,581,086
[45] Date of Patent: Dec. 3, 1996

[54] INFRARED LIGHT CHAMBER FOR FLUID MEASUREMENT

[75] Inventor: Uri Ben-Menachem, Hod Hasharon, Israel

[73] Assignee: S.C.R. Engineers Ltd., Netanya, Israel

[21] Appl. No.: 510,498

[22] Filed: Aug. 2, 1995

[51] Int. Cl.⁶ .......................... G01N 21/00; G01N 21/26
[52] U.S. Cl. ................ 250/343; 250/338.1; 250/339.06; 250/339.12; 250/340; 250/345
[58] Field of Search ............................... 250/343, 339.12, 250/338.1, 339.06, 340, 345, 349

[56] References Cited

U.S. PATENT DOCUMENTS

| | | | |
|---|---|---|---|
| 3,795,810 | 3/1974 | Conley et al. | 250/343 |
| 4,118,625 | 10/1978 | Underwood | 250/343 |
| 4,210,809 | 7/1980 | Pelavin | 250/343 |
| 4,495,417 | 1/1985 | Hohensang | 250/343 |
| 4,902,896 | 2/1990 | Fertig, Sr. et al. | 250/343 |
| 5,116,119 | 5/1992 | Brayer | 356/28 |
| 5,124,553 | 6/1992 | Hilliard et al. | 250/339.12 |
| 5,225,679 | 7/1993 | Clarke et al. | 250/339.12 |
| 5,239,860 | 8/1993 | Harris et al. | 250/339.12 |
| 5,412,581 | 5/1995 | Tackett | 250/339.12 |

OTHER PUBLICATIONS

Sigma-Aldrich Catalog; Spectroscopy Products; Cover Pages and pp. 2108, 2109; (1995).

*Primary Examiner*—Constantine Hannaher
*Assistant Examiner*—Virgil Orlando Tyler
*Attorney, Agent, or Firm*—Edward Langer

[57] ABSTRACT

A measurement chamber for measuring the quantity and composition of liquids, fabricated of a uniform semi-transparent material for illumination using infrared light. The chamber construction alleviates the problem of bypass light via the side walls of the chamber, and the construction is simple and suitable for mass production.

10 Claims, 1 Drawing Sheet

INFRARED LIGHT CHAMBER FOR FLUID MEASUREMENT

FIELD OF THE INVENTION

The present invention relates to instrumentation, and more particularly, to a chamber used for carrying out measurements on liquids by infrared light.

BACKGROUND OF THE INVENTION

Measurement chambers are used for carrying out measurements on liquids using infrared light, to obtain information on the quantity of liquid and its composition. These chambers are based on a transmitter which emits light on one side of the chamber, and a receiver which receives the light after passage through the liquid, on the other side of the chamber.

An estimation of the quantity of liquid in the chamber is obtained by measurement of the attenuation of light in passage through the liquid filling the chamber. An approximation of the composition of the liquid is achieved by analysis of the attenuation in the spectral domain. Since the different components of the liquid have attenuations dependent on the wavelength, it is possible to find the percentage of each component as a portion of the liquid.

Measurement chambers can be classified into two types:

1) Static—the measurement is achieved when the liquid is static in the measurement chamber. These chambers, known as spectroscopy chambers or spectrophotometer cuvets (available from Sigma Chemicals Corp. USA), are used in chemistry laboratories for spectral analysis of the material components;

2) Dynamic—here the measurement of liquid is achieved during movement. Such a chamber is used in milk flow meters, where an estimation of the quantity of milk in the pipe is achieved by measurement of the attenuation of the infrared light, as described in U.S. Pat. No. 5,116,119 to Brayer.

There are two types of measurement chambers in use today. The first type are transparent measurement chambers, in which the entire chamber is made of material transparent to infrared light. The major problem of this method of measurement is that even when the chamber is filled with fluid, light can pass through the side walls of the chamber (bypass light). To the extent that the transparency of the material to infrared light is low, then the situation is that almost all of the light received in the measurement area is bypass light that does not pass through the liquid at all. This phenomenon causes problems in the dynamic measurement range. For example, if 99.9% of the light is bypass light and one is interested in measuring the reduction with an accuracy of 0.1%, then the general required accuracy is 0.0001%. This level of measurement accuracy is very costly to obtain.

If the measurement is static, the situation can be improved by building a chamber having a small cross-sectional area such that even if the transparency of the liquid is low, it is possible to pass light through a thin layer of the liquid. This is not possible in dynamic measurements where there is a need to maintain continuous flow and high supply rate, since a small cross-sectional area would obstruct the continuous flow.

The second type of measurement chamber is a compound chamber which uses two materials, one transparent to illumination and the second opaque. The chamber is made of opaque material having implanted therein windows of transparent material. This construction insures passage of light via the liquid without the bypass phenomena. Disadvantages of the method include the high degree of manufacturing complexity, the need to use two materials, and the problem of sealing at the connection areas.

Therefore, it would be desirable to provide a simple measurement chamber which does not have bypass light problems.

SUMMARY OF THE INVENTION

Accordingly, it is a principal object of the present invention to overcome the problems associated with prior art measurement chambers and provide a method of constructing a measurement chamber using infrared light which does not suffer from the problem of bypass light via the sides, is simple and suitable for mass production.

In accordance with a preferred embodiment of the invention, there is provided a measurement chamber for liquids comprising a chamber fabricated of a uniform semi-transparent material for illumination.

Other features and advantages of the invention will become apparent from the following drawings and description.

DETAILED DESCRIPTION OF THE PREFERRED EMBODIMENT

Figure 1:
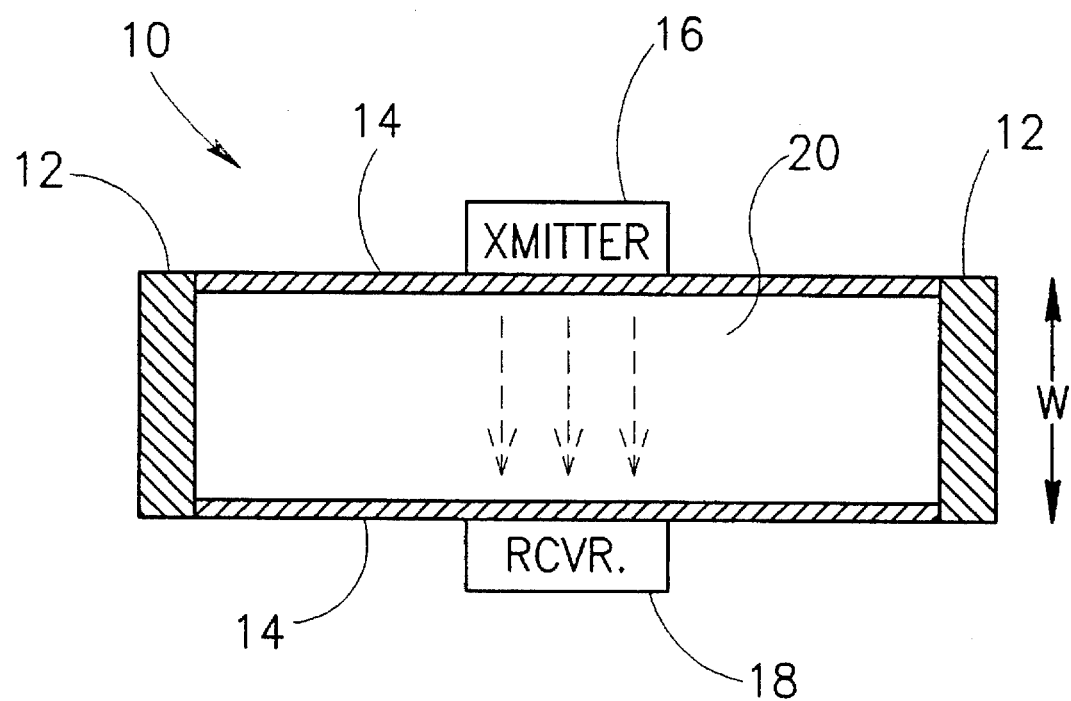
FIG. 1 is a top cross-sectional view of a measurement chamber constructed and operated in accordance with the present invention.

Referring now to FIG. 1, there is shown a top cross-sectional view of a measurement chamber 10, constructed and operated in accordance with a preferred embodiment of the present invention. Measurement chamber 10 is constructed of a uniform material and comprises end walls 12 and central walls 14, an infrared light transmitter 16, and infrared light receiver 18. The width of chamber 10 is denoted as W in FIG. 1, and the arrows show the direction of illumination.

The operation of the measurement chamber 10 is now described. Light emitted by transmitter 16 passes through central walls 14, and through the liquid 20 being measured, which fills chamber 10. The light is incident on receiver 18, and in addition, may pass via end walls 12 and also be received at 18.

In accordance with the principles of the present invention, chamber 10 is constructed of material which is semi-transparent to infrared light, based on three construction rules:

1) the entire chamber 10 is constructed of uniform material semi-transparent to infrared light with a desired attenuation factor;

2) the thickness of central walls 14 and the transparency of the material are chosen such that a high percentage of illumination will penetrate them;

3) the width (W) of chamber 10 is chosen such that a small percentage of illumination can pass through the end walls 12.

By establishing the following three parameters:

a) the degree of transparency of the material;

b) the thickness of central walls 14; and c) the width of chamber 10, it is possible to control the ratio between the percentage of illumination passing through central walls 14 to receiver 18, and the percentage of light passing through end walls 12 to receiver 18.

In an experimental measurement chamber 10, in which the thickness of central walls 14 was chosen to be 1 millimeter and the width W of chamber to be 10 millimeters, a ratio of 1:1000 was obtained between the bypass light illumination (via end walls 12) and the direct illumination via central walls 14.

The exact construction of measurement chamber 10 does not have to be in conformity with FIG. 1. The essential details for construction of the invention are:

use of uniform semi-transparent material;

thin thickness in transmission and reception areas;

provision of a long path for light passage through semi-transparent material with a desired attenuation factor to bypass the liquid.

One method of producing the semi-transparent material is to control the amount of color pigment or dye used during production of the plastic material.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

I claim:

1. A chamber for measuring the quantity and composition of a liquid contained therein, said chamber comprising:

a housing fabricated of semi-transparent material having a desired attenuation factor and having at least two opposing sides each associated with, respectively, at least one light transmitter and at least one light receiver, said housing having a pair of oppositely-facing end walls, such that when light is directed from said at least one light transmitter to said at least one light receiver through the liquid, a majority portion of the light passes via the liquid to provide an indication of the quantity and composition of the liquid, with a minimum amount of light passing via said end walls.

2. The chamber of claim 1 wherein said opposing housing sides comprise walls having a thickness, said housing has a cross-sectional area allowing a desired liquid flow rate, and the liquid has a transparency, said wall thickness, cross-sectional area and liquid transparency being chosen to maximize light passage via the liquid, without obstructing liquid flow.

3. The chamber of claim 1 wherein said semi-transparent material is plastic having an attenuation factor dependent on the amount of color pigment used in its production.

4. The chamber of claim wherein said light is infrared and near-infrared.

5. The chamber of claim 1 having a plurality of light transmitters and light receivers on opposing housing sides.

6. The chamber of claim 1 wherein the liquid is milk.

7. A method for measuring the quantity and compsosition of a liquid contained therein, said method comprising the step of directing light through a housing fabricated of semi-transparent material having a desired attenuation factor and having at least two opposing sides each associated with, respectively, at least one light transmitter and at least one light receiver, said housing having a pair of oppositely-facing end walls, such that when light is directed from said at least one light transmitter to said at least one light receiver through the liquid, a majority portion of the light passes via the liquid to provide an indication of the quantity and composition of the liquid, with a minimum amount of light passing via said end walls.

8. The method of claim 7 wherein said opposing housing sides comprise walls having a thickness, said housing has a cross-sectional area allowing a desired liquid flow rate, and the liquid has a transparency, said wall thickness, cross-sectional area and liquid transparency being chosen to maximize light passage via the liquid, without obstructing liquid flow.

9. The method of claim 7 wherein said light is infrared and near-infrared.

10. The method of claim 7 wherein the liquid is milk.

* * * * *